(12) United States Patent　　(10) Patent No.: US 7,944,562 B2
Schwarz　　(45) Date of Patent: May 17, 2011

(54) DEVICE AND METHOD FOR THE TOPOGRAPHICAL DETERMINATION OF SURFACE PROPERTIES

(75) Inventor: Peter Schwarz, Koenigsdorf (DE)

(73) Assignee: BYK-Gardner GmbH, Geretsried (DE)

( * ) Notice: Subject to any disclaimer, the term of this patent is extended or adjusted under 35 U.S.C. 154(b) by 266 days.

(21) Appl. No.: 11/835,419

(22) Filed: Aug. 8, 2007

(65) Prior Publication Data

US 2008/0034602 A1　Feb. 14, 2008

(30) Foreign Application Priority Data

Aug. 11, 2006　(DE) ................. 10 2006 037 681

(51) Int. Cl.
*G01N 21/00*　(2006.01)
(52) U.S. Cl. .............. 356/445; 356/237.1; 356/237.2
(58) Field of Classification Search .......... 356/445–448, 356/601–622
See application file for complete search history.

(56) References Cited

U.S. PATENT DOCUMENTS

| | | | | |
|---|---|---|---|---|
| 5,311,286 A | * | 5/1994 | Pike | 356/605 |
| 5,596,412 A | * | 1/1997 | Lex | 356/613 |
| 5,684,582 A | * | 11/1997 | Eastman et al. | 356/328 |
| 6,597,437 B1 | * | 7/2003 | Kongable | 356/3.01 |
| 7,227,648 B2 | * | 6/2007 | Weinhold | 356/601 |
| 7,391,518 B1 | * | 6/2008 | Schwarz et al. | 356/446 |
| 7,495,208 B2 | * | 2/2009 | Czarnek et al. | 250/234 |
| 7,566,894 B2 | | 7/2009 | Lex | |
| 2003/0137673 A1 | * | 7/2003 | Cox et al. | 356/601 |

FOREIGN PATENT DOCUMENTS

DE　10 2004 037 04 A1　3/2006

* cited by examiner

*Primary Examiner* — Michael P Stafira
(74) *Attorney, Agent, or Firm* — Oppedahl Patent Law Firm LLC

(57) ABSTRACT

The invention relates to a portable device (1) for the determination of surface properties with a measurement apparatus (10) which directly determines locally the topography of a surface (8) under investigation and issues at least one measured value that is characteristic of this local topography, and with a processor apparatus which, taking account of a multiplicity of initial measured values, issues at least one result value characteristic of the global topography of the surface.

18 Claims, 2 Drawing Sheets

DEVICE AND METHOD FOR THE TOPOGRAPHICAL DETERMINATION OF SURFACE PROPERTIES

BACKGROUND

The present invention relates to a device and a method for the determination of surface properties.

The invention is described with reference to painted surfaces, in particular to the surfaces of motor-vehicle bodywork. It is, however, pointed out that the present invention may also be used in the case of other surfaces.

In the case of numerous technical products, the quality of the visible surface is a crucial feature of the overall impression of the product.

In general, the visual impression of surfaces is decisively influenced by their quality, e.g. their colour, evenness, gloss, orange peel, Distinctness Of Image (DOI), etc. It is, in particular, the evenness or unevenness of the surface that here plays a critical role in respect of its visual impression.

Motor vehicles are usually provided with high-gloss paintwork, the gloss rating of which is generally vastly superior to the gloss rating of other surfaces, e.g. furniture surfaces and the like. The high gloss of the paints used and the relatively large surfaces demand extremely careful preparation of the surfaces to be coated, and very careful application of a base coat. Known from the prior art are devices that, in order to identify quality defects in painted bodywork surfaces, enable an objective characterisation or evaluation of surfaces by analysis of light radiated onto them. These devices make it possible e.g. to detect and quantitatively evaluate unevennesses in the paint layers.

Any unevenness of surfaces is determined by many different factors, such as the mean deviation from an ideally smooth surface, periodicities of individual deviations, etc. In the industrial manufacture of motor-vehicle surfaces or bodywork, a requirement exists to characterise or classify unambiguously any unevenness occurring, and/or the visual impression brought about by such unevenness.

The paints normally used in the automotive industry exhibit not just an external paint layer, but also base coats located beneath this external paint layer. In order to produce final layers of satisfactory quality, it is necessary to check the quality of the relevant base coats too. However, the problem then occurs that these base coats reflect light radiated onto them relatively weakly, and any evaluation of this base coat is therefore extremely complex. Known from DE 10 2004 037 040 A1 is a device in which a light-radiating apparatus radiates light beams in infrared-range wavelengths onto the surface. The use of infrared light ensures that sufficient light is reflected to enable evaluation to take place.

Using this apparatus, conclusions about unevennesses in the base coat are drawn by means of the reflected light. In other words, the base coat is evaluated not directly but indirectly using the reflected light or the directions of the reflected light. With a multiplicity of base coatings, however, even the use of infrared light does not enable evaluation, since even this is reflected too weakly.

Also known from the prior art are roughness measuring devices, which mechanically scan a surface and emit characteristic values for its roughness. These devices are, however, stationary and extremely cumbersome to operate, making them unusable for the examination of e.g. paints.

It would therefore be desirable to create a system and a device for characterising the visual impression of surfaces, which device may be used, in particular, on weakly reflective surfaces. This system is to be simple to operate and portable, in order that it can be used for diverse applications.

SUMMARY OF THE INVENTION

The portable device according to the invention for determining surface properties is equipped with a measurement apparatus which directly determines locally the topography of a surface under investigation and issues at least one measured value that is characteristic of this local topography. Also provided is a processor device which, taking account of a multiplicity of initial measured values, issues at least one result value characteristic of the global topography of the surface.

To be understood as topography in the context of the present description are, in particular, existing surface unevennesses. What is meant by the local determination of topography is that the height positions are in each case determined for individual points on the surface. The local determination constitutes the difference in relation to devices known from the prior art, such as layer-thickness measurement devices, which in each case issue an integral layer thickness for a particular area of the surface.

On the basis of a multiplicity of measured values for the local topography, the processor device determines a global topography of the surface. A representation of an entire surface and of its unevenness can be achieved in this manner.

In the case of the methods known from the prior art, the topography of the surface is not directly determined, but only the effects of the topography on a reflected light beam. In other words, the reflected light beam is recorded and conclusions are drawn about existing surface unevenness. Conversely, in the method according to the invention, the topography of the surface is directly determined and, using this topography, conclusions are drawn as to the visual impression that a coating applied to a base coat with this topography will create. The topography can also be directly evaluated and conclusions drawn as to the quality of the base coat overall.

In an exemplary embodiment, the device is equipped with at least one movement apparatus, which, during a measurement to determine the surface properties, remains in contact with the surface at least sectionwise, and by means of which the device can be moved, e.g. rolled, relative to the surface. This embodiment makes the use of portable equipment for examining base coats possible. This movement apparatus may, for example, comprise at least one or more wheels mounted on the device, although rotatable rubber tracks are also possible as the movement apparatus or gliding elements.

In an exemplary embodiment, the measurement apparatus is equipped with a light source, which radiates light with a multiplicity of different wavelengths onto the surface to be examined. Ideally, white light is used, i.e. a continuum with a multiplicity of wavelengths, e.g. from the ultraviolet to the near-infrared range, is emitted onto the surface. However, light with a plurality of discrete wavelengths could also be used. The light source for the light preferably radiates the light onto the surface essentially in a perpendicular direction. In this manner, the luminous efficiency of light still reflected can be increased. In general, even the very lowest degrees of surface reflection will suffice for this measurement apparatus.

In a further embodiment, a chromatic lens apparatus is disposed between the light source and the surface. By means of this chromatic lens apparatus, the components of the white light are dispersed along its optical axis, i.e. the focal points of the individual components of the white light change as a function of the particular wavelengths.

In a further exemplary embodiment, the measurement apparatus is equipped with a spectrometer. To be more precise, the light radiated onto the surface is reflected and directed in the direction of the spectrometer. Depending on the topography or the height of the coating, different colour components of the light will herein preferentially reach the spectrometer. In this manner, the topography of the surface can be determined via the wavelength of the radiated light reaching the spectrometer. This is explained more fully with reference to the Figures.

Instead of a spectrometer, CCD chips or other elements which enable analysis of the spectral components of the light impinging on them could also be used.

Instead of the optical variants described here, however, other variants would also be possible for the recording of the topography by high-sensitivity resolution, e.g. a so-called Hommel tester or other profilometers that determine, e.g. inductively, the topography of the surface.

The results value characteristic of the global topography of the surface is preferably a statistical value derived from a group of statistical values containing mean values, scatter, medians, spread, minima, maxima, absolute deviations, standard deviations, variances, Fourier coefficients, combinations of these, etc. Especially preferred for the characteristic value is a Fourier coefficient or locally filtered measured values.

Provided in a further exemplary embodiment is a memory apparatus in which a multiplicity of initial measured values are stored. This memory apparatus enables the recording of a profile of the surface under examination. Additionally advantageously provided is a distance meter to determine the length of a distance that the device is moved relative to the surface under examination. The distance meter is preferably coupled with the movement apparatus, e.g. with a wheel, and emits signals characteristic of the distance covered. Each measured value for the topography can thereby be assigned to a corresponding distance-measured value, and a diagram or representation in which the location on the surface relative to a topography value is plotted can be compiled in this manner. The user can thereby guide the device over the surface, and receives information concerning its topography. It can simultaneously be ensured by the movement apparatus that the space between the device and the surface remains constant.

Provided in a further exemplary embodiment are a further light-radiating apparatus, which directs light onto the surface under examination, and a light-radiation detector apparatus, which records the light reflected and/or scattered by the surface, and emits a signal characteristic of the surface. On the one hand, this further light-radiating apparatus can be used to enable the equipment to be used both for base coats and for further paint coats, and, on the other, it is also possible to use the values recorded by the second light-radiation detector apparatus to correct or verify the values emitted by the measurement apparatus.

The present invention is further directed at a method for the examination of surface properties. In a first step, an initial measured value is directly determined in the measurement apparatus, wherein the initial measured value is characteristic of a local topography of a surface to be examined. In a second step, an initial results value characteristic of the global topography of the surface is issued, wherein a multiplicity of initial measured values are taken into account to determine this characteristic results value. Preferably issued in addition to the initial characteristic results value is at least a second characteristic results value, wherein this second characteristic results value is also determined by taking account of the initial measured values. It is especially preferred for the two characteristic measured values to be Fourier coefficients or locally filtered measured values with which a surface structure of the surface under examination is analysed.

It is preferred, therefore, for a statistical variable determined over at least some of the initial measured values for characterisation of the surface to be the characteristic results value. It is especially preferred for a measurement apparatus of the type described above to be used for the method according to the invention.

In a further advantageous method, it is also possible to plot a multiplicity of initial measured values in a common reference system. It is possible here to plot the measured values in e.g. a system of Cartesian coordinates in order to obtain a representation of the topography in this manner. Here, for example, the plane of the surface could be shown in the X and Y directions and the relevant height value in the Z direction. Other coordinate systems could also be used, however.

Preferably, a multiplicity of initial measured values is evaluated using a Fourier transformation or a spatial-frequency filter. This is explained more fully with reference to the Figures.

Preferably, the measurement apparatus is moved relative to the surface to be examined and the topography of the surface is determined in this manner as described above. The measurement apparatus may also be disposed on a movable arm of a robot and thus moved relative to the surface. A control system for this robot could here also determine the relevant location of the device relative to the surface.

DESCRIPTION OF THE DRAWINGS

Further advantages and embodiments are described in the accompanying drawings, wherein.

DETAILED DESCRIPTION

Figure 1:
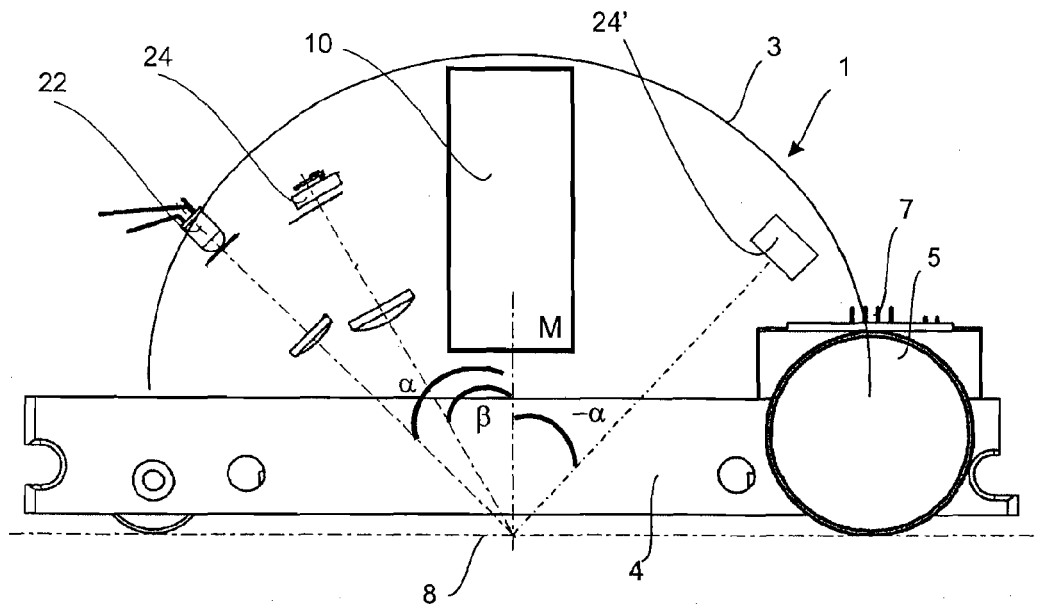
FIG. 1 shows a device according to the invention for the determination of surface properties.

FIG. 1 shows a schematic representation of a device 1 according to the invention for the determination of surface properties. This device is equipped with a housing 3 in which is disposed inter alia a measurement apparatus 10, which directly determines locally the topography of the surface 8 under examination. With this embodiment, the measurement apparatus 10 is disposed perpendicularly above the surface 8. In addition, the device is equipped with wheels 5 disposed on a base 4 so that they can be moved relative to the surface 8 under examination. A processor unit 7 contains a distance meter, which determines the length of a distance covered by the device relative to the surface 8.

Also provided in the embodiment shown in FIG. 1 is a further light-radiating apparatus 22, and a light-radiation detector apparatus 24. The light-radiating apparatus 22 emits radiation and, in particular, light, onto the surface 8, and the light reflected back by the surface is recorded by the light-radiation detector apparatus 24. Measurement is here in the direct reflection, especially in the case of measuring orange peel. This is illustrated in FIG. 1 by the light-radiation detector apparatus 24', shown with a broken line, which is drawn at an angle $-\alpha$ relative to the mid perpendicular. In the embodiment shown here, the light-radiating apparatus 22 is disposed at an initial angle $\alpha$ relative to the mid perpendicular M and the light-radiation detector apparatus 24 is disposed at an angle −α relative to the mid perpendicular M.

Instead of the embodiments shown here, however, a plurality of the light-radiating apparatus 22 and/or a plurality of the light-radiation detector apparatus 24 may be disposed at different angles α or β relative to the mid perpendicular. Such light-radiating apparatus and light-radiation detector apparatus serves, in particular, for surfaces that reflect back a higher proportion of radiated light.

Figure 2:
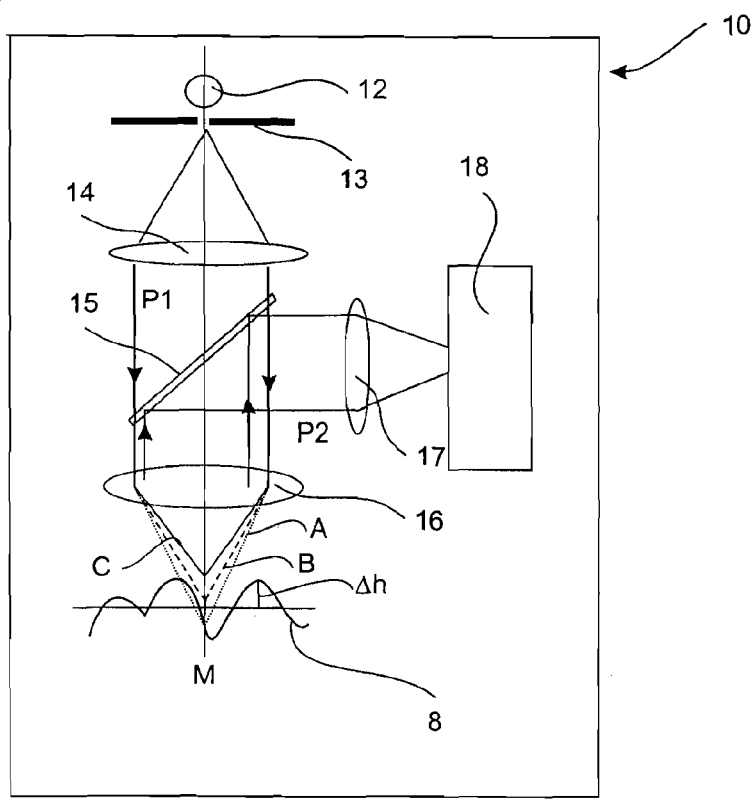
FIG. 2 shows a schematic representation of the measurement apparatus.

FIG. 2 shows a schematic representation of the measurement apparatus 10 from FIG. 1. This is equipped with a light source 12, which emits white light or generally, a multiplicity of wavelengths. Reference number 13 relates to a diaphragm, which causes a strong divergence of the light emitted by the light source 12. The light is then directed by a first lens 14 and directed along arrow P1 onto a second lens 16. This second lens is a chromatic lens or a chromatic objective lens system.

The so-called chromatic aberration is a long-known imaging error of optical lenses which depends on the wavelength or colour of the light. Owing to the dependence of the refractive index on the wavelength, convergent lenses exhibit a shorter focal distance for blue light than for e.g. red light. Light of different wavelengths is therefore focussed at different points, and colour fringing occurs.

Owing both to their position on the optical axis and to their imaging variable in the focal plane, the images of the three primary colours differ from each other. A distinction is therefore made in respect of chromatic aberration between lateral chromatic error (axial deviation) and transverse chromatic error. This lateral chromatic error is exploited by the present measurement apparatus 10 in order to determine the contour or topography of the surface 8. The white light exits from the lens 16, wherein shown here by way of example are three light beams A, B and C, which are focussed at different focal points. Reference letter C here signifies a beam of short wavelength, reference letter B a beam of medium wavelength and reference letter A a component of long wavelength. Depending on the distance between the surface and the lens, different colour components are focussed onto the surface 8.

Especially strongly reflected by the surface 8 are those components having their focus in the point of incidence on the surface, as with component A in FIG. 2. The individual components are reflected back as shown by arrows P2, and directed via the semi-reflecting mirror 15 and a lens 17 onto a spectrometer 18. This spectrometer 18—e.g. a monochromator—analyses the particular wavelength with the highest intensity. The height Δh of the surface 8 relative to a specific base level, e.g. relative to an ideally smooth surface, can be concluded on the basis of this wavelength. The topography of the surface 8 can be determined in this manner.

It would, however, also be possible to use special lens facilities, such as cylindrical lenses, in order to ensure that the light incident upon the surface strikes the surface not in punctiform fashion but linearly. In this manner, not just linear elements but planar elements could be scanned with a relative movement of the device relative to the surface. A plurality of measurement apparatuses could also be disposed adjacent to one another in a line located essentially perpendicular to the plane of the Figures in FIG. 1.

By comparison with variants known from the prior art, the determination herein is of the topography of the surface directly, and not, as has been usual hitherto, just of the effects of a topography of this kind on reflected light.

It is pointed out, however, that the topography of the surface can also be established using other high-resolution methods, e.g. by using inductive effects. Here again, it would be possible to scan planar elements rather than linear ones.

Figure 3:
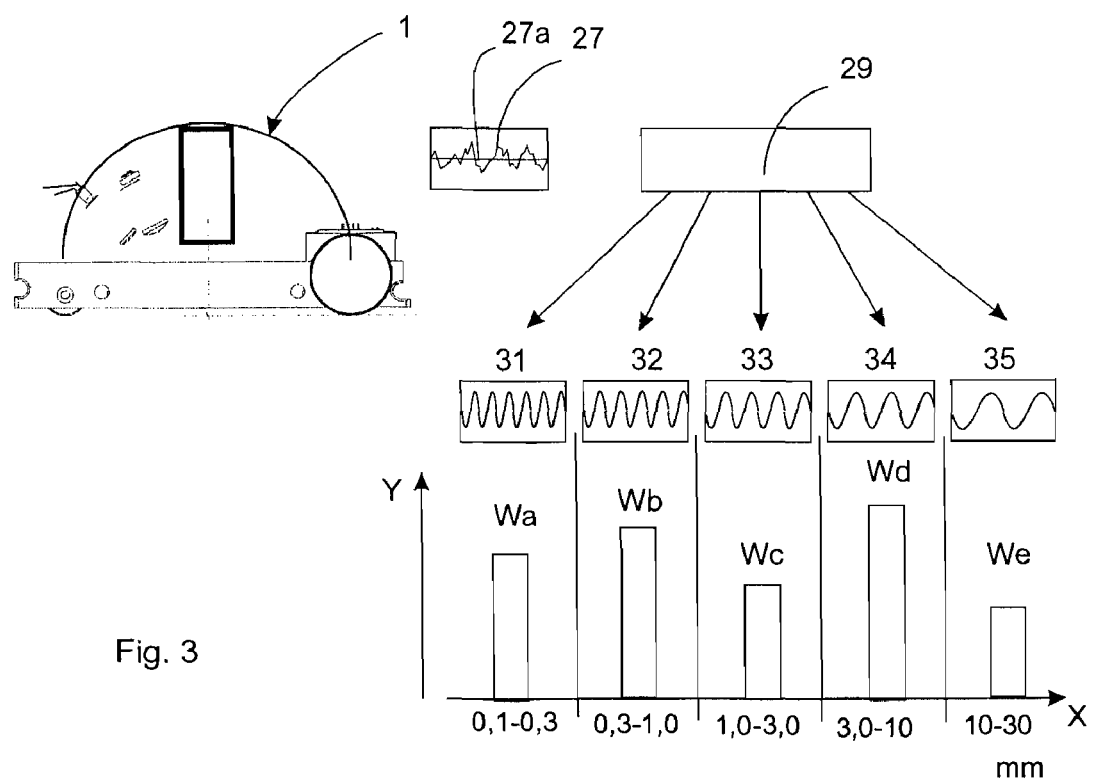
FIG. 3 shows a schematic representation of the evaluation method.

In FIG. 3, the method for evaluating the visual characteristic is explained. The topography is here issued by the device 1 together with the distance covered relative to the device. This produces e.g. the measurement graph 27, with which the surface topography is plotted in one direction relative to the distance. Reference number 27*a* here relates to an ideally smooth surface against which the measurement graph 27 deviates. This topography measurement graph is then evaluated with an evaluation apparatus 29, preferably undertaking a Fourier transformation or local filtration.

It is especially preferred for a plurality of weighted local filters to be used, i.e. for the evaluation, the measurement graph is analysed according to different wavelength ranges, and optimally adapted through appropriate weighting of the factors of the different wavelengths.

In general, the visibility of structures depends on the observation distance. The greater this distance, the smaller objects will appear. Structures with dimensions of 10 to 30 mm can be best observed from a distance of ca. 3 m. Fine structures in the range 0.1 mm to 1 mm can be recognised only at a short distance.

The resolvable pattern size also depends on the observation distance. Very fine structures located below the resolution capability of the human eye (ca. 0.1 mm) can no longer be perceived, even at very short distances, as light/dark patterns. As a result, there is a reduction in the image forming quality (IFQ). At an observation distance of 3 m, structures between 1 mm and 3 mm can scarcely still be resolved as waviness, but they affect the appearance.

Here, by differing filtration, a division of the wavelengths is undertaken, namely into an extremely short-wave range Wa with a periodicity between 0.1 and 0.3 mm, a short-wave range Wb of 0.3 to 1 mm, a range of medium wavelength Wc of 1 to 3 mm, a range of longer wavelength Wd with 3 to 10 mm and a longwave range We of 10 to 30 mm.

Instead of the division into five components described here, however, more or fewer components could also be provided, as a result of which ultimately the measurement result 27 can be approximated with greater or lesser accuracy. Plotted along the y-axis, as stated, is the variable of the resultant individual Fourier coefficients or components of the local filtration, i.e. amplitudes Wa, Wb, Wc, Wd and We. These, specifically components of the local filtration, or variances of the amplitudes of the ranges Wa to We filtered according to ranges 31 to 35, are the characteristic variables mentioned above. The terms "Fourier coefficients" and "components of the local filtration" are used synonymously in the context of the present description.

The range of 0.1 to 30 mm quoted above could be further expanded but it has proved true that wavelengths below 0.1 mm and above 30 mm do not play any decisive role in the determination of surface properties. In the context of the embodiment example shown here, only the components of local filtration, or variances, Wb, Wc and Wd, with which the actual surface characteristic can be described sufficiently accurately, are taken into account. In the case of other applications, e.g. for surfaces exhibiting different characteristics, the examination could rely on different Fourier coefficients or components of local filtration, such as Wc, Wd and We. The wavelength ranges assigned to the individual Fourier coefficients/components of the local filtration could also be differently determined, e.g. assignment of the wavelength range 30 to 100 mm to the Fourier coefficient or components of the local filtration We.

In addition to the components of local filtration or variances shown here, the waviness of the surface derived overall is also determined as an average (not shown). To this end, in a preferred application, the entire measurement range 27 is evaluated, and an average value for the deviations determined. This evaluation may take place over all wavelength ranges 31 to 35. In addition, individual ranges may also be evaluated and weighted more or less strongly in relation to other ranges, and those wavelength ranges located below the range Wa or above the range We may also be taken into account.

These individual, established variables, such as Wa to We, may be plotted again for different surfaces. In a further embodiment, it is also possible to form certain quotients from this Fourier coefficient/components of the local filtration, and to plot them in a further system of coordinates. Thus it is possible in a coordinate system to plot on one axis the ratio of the shortwave proportion, represented by the coefficient Wb, to the longwave proportion, represented by the Fourier coefficient Wd, specifically the value Wd characteristic of this filter range. By means of these ratios, the appearance of a finished surface, i.e. once a further coat of paint has been applied on top of a base coat, can also be predicted. Similar ratios can also be created between the values Wd and Wc, in order to obtain information as to the appearance of the finish-painted surface when this measured surface has been painted with a top coat. However, analysis of the individual coefficients alone enables prognoses as to the finished paintwork or information as to whether the subsequent painting of this surface will be satisfactory. In addition, it is also possible to examine the finished paintwork during a further measurement. So the method according to the invention and the device according to the invention serve precisely for undertaking measurements on a base coat with low reflective properties.

| List of reference characters | |
|---|---|
| 1 | Device for the determination of surface properties |
| 3 | Housing |
| 4 | Base |
| 5 | Wheel |
| 7 | Processor unit |
| 8 | Surface |
| 10 | Measurement apparatus |
| 12 | Light source |
| 13 | Diaphragm |
| 14 | First lens |
| 15 | Semi-reflecting mirror |
| 16 | Second lens (chromatic) |
| 17 | Lens |
| 18 | Spectrometer |
| 22 | Light-radiating apparatus |
| 24, 24' | Light-radiation detector apparatus |
| 27 | Measurement graph |
| 27a | Ideally smooth surface |
| 29 | Evaluation apparatus |
| 31, 32, 33, 34, 35 | Wavelength ranges |
| Wa, Wb, Wc, Wd, We | Weighted spatial-frequency coefficients |
| A, B, C | Light beams |
| α, β, -α | Angles |

Those skilled in the art will have no difficulty devising myriad obvious improvements and variants without departing in any way from the invention, all of which are intended to be encompassed within the claims which follow.

The invention claimed is:

1. A portable device (1) for the determination of surface properties of motor vehicle bodywork with a housing equipped with a processor apparatus and a measurement apparatus (10) which directly determines locally the topography of a surface (8) under examination and issues at least one measured value that is characteristic of this local topography, the surface (8) under examination being a surface arranged side by side the portable device (1), when the measurement apparatus (10) determines the topography thereof, and the processor apparatus which, taking account of a multiplicity of initial measured values, issues at least an initial result value characteristic of the global topography of the surface and draws conclusions to the visual impression that a coating applied to a base coat with the determined topography will create, wherein disposed on the device is at least one movement apparatus having at least one wheel which remains in contact with the surface at least sectionwise, and by means of which movement apparatus the device can be moved relative to the surface.

2. The device of claim 1 wherein the measurement apparatus is equipped with a light source (3) which radiates light with a multiplicity of different wavelengths onto the surface under examination.

3. The device of claim 1 wherein the light source (12) radiates the light onto the surface (8) in an essentially perpendicular direction.

4. The device of claim 2 wherein a chromatic lens apparatus (16) is disposed between the light source (12) and the surface (8).

5. The device of claim 1 wherein the measurement apparatus is equipped with a spectrometer (18).

6. The device of claim 1 wherein the characteristic results value is a statistical value derived from a group of statistical values comprising mean values, scatter, medians, spread, minima, maxima, absolute deviations, standard deviations, variances, Fourier coefficients, locally filtered variables, and a combinations of these.

7. The device of claim 1 wherein the device is equipped with a distance meter to determine the length of a distance that the device is moved relative to the surface (8) under examination.

8. A method for the examination of surface properties of motor vehicle bodywork comprising the steps of:
directly determining an initial measured value with a portable device (1) for examination of surfaces, comprising a housing equipped with a processor apparatus and a measurement apparatus (10), wherein the initial measured value is characteristic of a local topography of a surface to be examined and which is arranged side by side the portable device (10), when the measurement apparatus (10) determines the topography thereof;
issuing an initial results value characteristic of the global topography of the surface, wherein a multiplicity of initial measured values are taken into account by the processor apparatus to determine this characteristic results value; and
drawing conclusions to the visual impression that a coating applied to a base coat with the determined topography will create, wherein the device is moved relative to the surface by means of a movement apparatus which has at least one wheel and which remains in contact with the surface at least sectionwise.

9. The method of claim 8 wherein in addition to the initial characteristic results value is at least a second characteristic results value, which is also determined by taking account of the initial measured values.

10. The method of claim 8 wherein a characteristic results value is a statistical variable determined over at least some of the initial measured values for characterisation of the surface.

11. The method of claim 8 wherein a multiplicity of initial measured values are plotted in a common reference system.

12. The device of claim 1, wherein the housing is equipped with a further light-radiating apparatus and a light-radiation detector apparatus.

13. The device of claim 12, wherein light emitted by the light-radiation apparatus is recorded by the light-radiation detector apparatus in the direct reflection.

14. The device of claim 3, wherein the measurement apparatus comprises a diaphragm, which causes a divergence of the light emitted by the light source.

15. The device of claim 5, wherein the components of the light are directed via a semi-reflecting mirror and a lens onto the spectrometer.

16. The device of claim 1, wherein one determined surface property is unevenness in a range between 0 mm and 5 mm.

17. A method for the examination of surface properties of motor vehicle bodywork comprising the steps of:
  directly determining an initial measured value with a portable device (1) for examination of surfaces, comprising a housing equipped with a processor apparatus and a measurement apparatus (10), wherein the initial measured value is characteristic of a local topography of a surface to be examined and which is arranged side by side the portable device (10), when the measurement apparatus (10) determines the topography thereof, and wherein the topography of the surface is determined via the wavelengths of light radiated from the surface;
  issuing an initial results value characteristic of the global topography of the surface, wherein a multiplicity of initial measured values are taken into account by the processor apparatus to determine this characteristic results value; and
  drawing conclusions to the visual impression that a coating applied to a base coat with the determined topography will create, wherein the device is moved relative to the surface by means of a movement apparatus which has at least one wheel and which remains in contact with the surface at least sectionwise.

18. A portable device (1) for the determination of surface properties with a housing equipped with a processor apparatus and a measurement apparatus (10) which directly determines locally the topography of a surface (8) under examination and issues at least one measured value that is characteristic of this local topography, the surface (8) under examination being a surface arranged side by side the portable device (1), when the measurement apparatus (10) determines the topography thereof, and the processor apparatus which, taking account of a multiplicity of initial measured values, issues at least an initial result value characteristic of the global topography of the surface and draws conclusions to the visual impression that a coating applied to a base coat with the determined topography will create, wherein the measurement apparatus is equipped with an element which enables an analysis of the spectral components of the light impinging on it to determine the topography of the surface wherein disposed on the device is at least one movement apparatus having at least one wheel which remains in contact with the surface at least sectionwise, and by means of which movement apparatus the device can be moved relative to the surface.

\* \* \* \* \*